United States Patent [19]

Kita et al.

[11] Patent Number: 4,980,483

[45] Date of Patent: Dec. 25, 1990

[54] METHOD FOR PRODUCTION OF MALEIMIDES

[75] Inventors: Yuichi Kita, Akashi; Masakazu Nakagawa; Hitoshi Kanei, both of Himeji; Akio Fukui, Fujisawa, all of Japan

[73] Assignee: Nippon Shokubai Kagaku Kogyo Co., Ltd., Osaka, Japan

[21] Appl. No.: 310,862

[22] Filed: Feb. 14, 1989

[30] Foreign Application Priority Data

Mar. 25, 1988 [JP] Japan .................. 63-69260

[51] Int. Cl.$^5$ .......................... C07D 207/448
[52] U.S. Cl. ........................ 548/548; 548/549
[58] Field of Search ............... 548/548, 549

[56] References Cited

U.S. PATENT DOCUMENTS

| | | | |
|---|---|---|---|
| 4,111,879 | 9/1978 | Mori et al. | 260/29.6 |
| 4,138,243 | 2/1979 | Bohner et al. | 548/549 |
| 4,171,302 | 10/1979 | Abblard et al. | 548/548 |
| 4,229,351 | 10/1980 | Kiefer et al. | 548/548 |
| 4,500,719 | 2/1985 | Oga et al. | 548/549 |
| 4,605,700 | 8/1986 | Lo-Khuc | 525/73 |
| 4,623,734 | 11/1986 | Kita et al. | |
| 4,786,738 | 11/1988 | Kita et al. | 548/549 |

FOREIGN PATENT DOCUMENTS

| | | |
|---|---|---|
| 0129125 | of 1984 | European Pat. Off. |
| 53-68770 | of 1978 | Japan . |
| 57-42043 | of 1982 | Japan . |
| 62-273952 | 11/1987 | Japan . |
| 1041027 | 9/1966 | United Kingdom . |

Primary Examiner—David B. Springer
Attorney, Agent, or Firm—Omri M. Behr

[57] ABSTRACT

A method for the production of a maleimide, which comprises effecting a former-stage reaction by adding maleic anhydride and a primary amine in amounts such that the molar ratio of said maleic anhydride to said primary amine is less than 1 under application of heat to a water-insoluble or water-immisible inert organic solvent containing an acid catalyst and subsequently carrying out a latter-stage reaction by adding to the reaction system maleic anhydride in an amount such that the molar ratio of the total amount of maleic anhydride to be added to said reaction system to the total amount of said primary amine added to said reaction system exceeds 1.

12 Claims, No Drawings

METHOD FOR PRODUCTION OF MALEIMIDES

BACKGROUND OF THE INVENTION

1. Field of the Invention:

This invention relates to a method for the production of a maleimide. More particularly, it relates to a method for the production of a maleimide by the reaction of maleic anhydride with a primary amine.

2. Description of the Prior Art:

Maleimides are compounds useful as raw materials for synthetic resins, medicines, and agricultural chemicals. Researches after methods for their produciton have long been under way. The most popular method of them all effects the production of maleimides by the dehydration cyclization of maleinamic acids with a dehydrating agent such as acetic anhydride. One version of this method is disclosed in U.S. Pat. No. 2,444,536. This method effects the production of maleimides by causing maleic anhydride to react upon amines thereby forming maleinamic acids and dehydration cyclizing and, at the same time, imidating the maleinamic acids in the presence of acetic anhydride and sodium acetate. This method, however, has the disadvantage that the imidation requires expensive acetic anhydride to be used in at least an equivalent relative to the maleinamic acid and the separation and recovery of the formed maleimide from the imidation reaction solution necessitates use of a large volume of water and, as the result, entails disposal of a large amount of an acetic acid-containing effluent at great expense. Thus, this method may will be called a too expensive method for commercial production of malemidies.

A method which has no use for such a chemical dehydration agent as acetic anhydride is disclosed in British Patent No. 1,041,027 and U.S. Pat. No. 3,431,276. This method effects the production of maleimides by thermally dehydrating and cyclizing maleinamic acids in conjunction with a solvent such as, for example, toluene, xylene, or chlorobenzene having a boiling point exceeding 80° C. and serving as a diluent and an acid catalyst such as sulfur trioxide, sulfuric acid, or orthophosphoric acid, and distilling the system thereby causing azeotropic expulsion of the consequently formed water in conjunction with the solvent. As compared with the method which uses acetic anhdyride, this method proves advantageous in that it does not require use of a large amount of such an expensive dehydrating agent as acetic anhydride and further that the formed maleimides are separated and recovered with ease. This method nevertheless has the disadvantage that the yield of the imidation is low as compared with that obtainable by the method using acetic anhdyride. This disadvantage is logically explained by a postulate that compared with the method which effects the imidation by the use of acetic anhydride, the method which effects the imidation by performing thermal dehydration in the specific solvent as described above involves a high reaction temperature and, therefore, tends to induce side reactions and inevitably manages to produce maleimides abounding with impurities and further that since maleimdies are thermally unstable, the maleimides produced at all are degenerated during the course of the reaction. Further, as a commercial process, this method is not ecconomically satisfactory, because it requires to use an expensive acid catalyst in a relatively large amount and, moreover, produces the maleimides in a low yield.

There is another method which, as disclosed in Japanese Patent Laid-Open SHO 53(1978)-68,770 and Japanese Patent Publication SHO 57(1978)-42,043, comprises causing maleic anhydride to react on amines in the presence of an organic solvent thereby forming maleinamic acids and subjecting the maleinamic acids as held in a state not isolated from the reaction system to dehydration and cyclization in the presence of such an aprotic polar solvent as dimethyl formamide or dimethyl sulfoxide and an acid catalyst. By this method, there is offered recognizable improvement in yield as compared with the second method described above. This method, however, has these disadvantages, that the cost of production of maleimides is high because expensive and highly toxic aprotic polar solvent such as dimethyl formamide is used in a large amount, that the solvent such as dimethyl formamide is degenerated by the action of an acid catalyst used in the reaction and, therefore, the solvent is lost greatly, and that since the aprotic polar solvent used in the reaction has a high boiling point, the solvent is removed from the produced malimides with great difficulty.

Japanese Patent Laid-Open SHO 60(1985)-11,465 and Japanese Patent Laid-Open SHO 62(1987)-273,952 disclose a method which produces a maleimide by subjecting maleic anhydride and an amine to condensation in a solvent in the presence of an acid catalyst. To be specific, this method effects the production of a maleimide by preparatorily charging a reactor with the maleic anhydride, the solvent, and the acid catalyst and adding the amine dropwise to the reaction system with the solvent kept refluxed thereby allowing the water formed by the reaction to be expelled as mixed with the solvent from the reaction system. This method, however, has a disadvantage that the maleic anhydride readily reacts with the water formed by the condensation and gives rise to maleic acid and the maleic aicd thermally induces the reaction of rearrangement and entails heavy by-production of fumaric acid.

As a result, the amount of the maleic anhydride to be actually consumed in the reaction is decreased and the yield of the maleimide to be produced is lowered proportionately. Further, the reaction performed under such conditions as described above entails various secondary reactions and forms the product aimed at in a very low yield. Moreover, since the by-produced fumaric acid is insoluble in the acid catalyst and the solvent, it is suffered to accumulate in the boundary between the two liquid layers possibly to an extent of obscuring the interface between the liquid layers. As a result, the separation of the reaction solution and the catalyst to be made after completion of the reaction is attained only with great difficulty. If the separation is carried out with great strain, the catalyst is suffered to mingle with the insoluble fumaric acid at a conspicuous sacrifice of the attributes of the catalyst. The catalyst recovered by the separation, therefore, is cannot be effectively reused in its unmodified form.

As described above, the methods heretofore proposed for the production of a maleimides have numerous problems and cannot be satisfactorily adopted on a commercial scale.

An object of this invention, therefore, is to provide a novel method for the production of a maleimides.

Another object of this invention is to provide a method which is capable of producing a maleimide safely, easily, and inexpensively in a high yield.

SUMMARY OF THE INVENTION

The objects described above are accomplished by a method for the production of a maleimide, which comprises effecting a former-stage reaction by adding maleic anhydride and a primary amine in amounts such that the molar ratio of the maleic anhydride to the primary amine is less than 1 under application of heat to a water-insoluble or water-immiscible inert organic solvent containing an acid catalyst and subsequently carrying out a latter-stage reaction by adding to the reaction system maleic anhydride in an amount such that the molar ratio of the total amount of maleic anhydride to be added to the reaction system to the total amount of the primary amine added to the reaction system exceeds 1.

We have continued a protracted study on the reaction of condensation of maleic anhydride and an amine in a water-insoluble or water-immiscible inert organic solvent in the presence of an acid catalyst. In this study, we have devoted a special attention to the search of reaction conditions which curb the occurrence of fumaric acid during the course of the reaction and permits production of a maleimide in a high yield and consequently leads to fulfilment of the objects described above.

It has been consequently found unexpectedly that the occurence of fumaric acid is curbed conspicuously by causing the reaction to proceed under conditions such that the amine is always in an excess amount in the reaction system relative to the amount of the maleic anhydride. It has been further found that under such reaction conditions as to permit heavy by-production of a 2-amino-N-substituted succinimide and this by-production causes a notable decline in the yield of the maleimide.

It has been found beyond all expectations that the 2-amino-N-substituted succinimide, on reacting with maleic anhydride, efficiently decomposes itself into a maleimide with high selectivity. This invention has been produced as a result. To be specific, this invention is directed to a method for the production of a maleimide by the reaction of condensation caused on maleic anhydride and a primary amine by heating the reactants in a water-insoluble or water-immiscible inert organic solvent in the presence of an acid catalyst, which method is characterized by carrying out a former-stage reaction by adding the maleic anhydride and the primary amine dropwise in such a manner as to meet the conditions of (1) into a reaction vessel containing in advance the organic solvent in combination with the acid catalyst and subsequently carrying out a latter-stage reaction by adding the maleic anhydirde in such a manner as to meet the conditions of (2) to the reaction system.

Maleic anhydride/primary amine (molar ratio) < 1  (1)

Total amount of maleic / Total amount of primary  (2)
anhydride added to the / amine added to the
reaction system             reaction system (molar ratio) > 1

In a method for the production of a maleimide by the reaction of condensation caused on maleic anhydride and a primary amine by heating the reactants in a water-insoluble or water-immiscible inert organic solvent in the presence of an acid catalyst, the salient feature of this invention resides in the fact that the by-production of fumaric acid can be efficiently curved and the production of the maleimide can be attained safely and easily by allowing the reaction of the maleic anhydride and the primary amine in the reaction system to be carried out in two stages with the ratio of the maleic anhydride to the primary amine in the reaction system varied in these two stages and the production can be accomplished in high yield by allowing the 2-amino-N-substituted succinimide formed by the secondary reaction to be decomposed into the maleimide with high selectivity.

EXPLANATION OF PREFERRED EMBODIMENT

Examples of the primary amine particularly useful as the raw material for the maleimide in this invention include methylamine, ethylamine, n-propylamine, isopropylamine, n-butylamine, sec-butylamine, isobutylamine, tert-butylamine, n-hexylamine, n-dodecylamine, allylamine, benzylamine, cyclohexylamine, aniline, nitroaniline, aminomonochloroaniline, dichloroaniline, toluidines, xylidines, and ethylanilines.

The organic solvent to be used in the present invention is desired to be capable of permitting the water formed by the reaction of dehydration and cyclization to be expelled from the reaction system through azeotropic distillation therewith, insoluble or immiscible in water, inert, and incapable of participating in the reaction. Examples of the organic solvent meeting this description are benzene, toluene, oil fractions boiling at temperatures in the range of 50° to 120° C., xylenes, ethyl benzene, isopropyl benzene, cumene, mesitylene, tert-butyl benzene, pseudo-cumene, trimethyl hexane, octane, tetrachloroethane, nonane, chlorobenzene, ethyl cyclohexane, oil fractions boiling at temperatures in the range of 120° to 170° C., m-dicyclobenzene, sec-butyl benzene, p-dichlorobenzene, decane, p-cymene, o-dichlorobenzene, butyl benzene, decahydronaphthalene, tetrahydronaphthalene, dodecane, naphthalene, cyclohexyl benzene, and oil fractions boiling at temperatures in the range of 170° to 250° C. From the standpoint of enabling this reaction to proceed smmothly under satisfactorily economic conditions, the amount of this solvent to be used in the reaction is in the range of about 1 to about 40 times, preferably 2 to 14 times (by weight), the amount of the primary amine used as a raw material.

Further, the solvent is selected on the condition that it should possess a boiling point suiting the prevalent reaction conditions in due consideration of the solubility of the maleimide, price, and ease of handling. When the separation of the maleimide and the solvent after completion of the reaction demands an important consideration, there are times when the reaction performed by the use of a solvent of a low boiling point under application of pressure may prove to be more advantageous.

The substance usable as the catalyst herein include inorganic or organic monobasic acids and polybasic acids such as sulfuric acid, p-toluenesulfonic acid, orthophosphoric acid, methaphosphoric acid, pyrophosphoric acid, benzenesulfonic acid, and trichloroacetic acid, and/or amine salts obtained by the neutralizing reaction of these acids with amines as raw materials for the production of maleimide, for example.

The catalyst may be used as deposited on a solid carrier.

Examples of the solid carrier to be used advantageously herein include natural minerals such as kaolins, clay, talc, chalk, quartz, bentonite, montmorillonite, and diatomaceous earth; synthetic minerals such as highly dispersed silicic acid, alumina, silicates, activated carbon, gypsum, iron oxide red, titanium dioxide, silica, silica-alumina, and zirconium oxide; and natural rocks such as calcite, marble, pumice, sepiolite, and dolomite.

Such an inorganic carrier is used in the form of powder, in the form of granules obtained by pelletizing and classifying the relevant substance, or in the form of a honeycomb.

It is also permissible to use an organic carrier. A granular carrier of polyfluorocarbon, polystyrene, or phenol resin can be effectively used. The catalysis is obtained with particularly desirable results when the carrier is made of such a porous substance as diatomaceous earth, silica gel or activated carbon. As typical examples of the cmmercially available carrier usable effectively herein include a product of diatomaceous earth (marketed by Showa Chemical Industry Co., Ltd. under trademark designation of "Radiolight") and products of silica gel (marketed by Fuji-Davison Chemical Co., Ltd. under trademark designations of "Carriact" "SYLOID," and "Microbead Silica Gel"), a product of silica gel (marketed by Wako-Junyaku Industry Co., Ltd. under trademark designation of "Wakogel"), and a product of activated carbon (marketed by Taiyo Kaken Co., Ltd. under trademark designation of "BAC".

The amount of the catalyst of the foregoing description to be used is in the range of 2 to 400 mol %, preferably 20 to 200 mol %, based on the amount of the primary amine to be used as an acid component, part or the whole of the acid destined to serve as the catalyst may be neutralized with an amine.

There are times when the reaction can be carried out, as disclosed in U.S. Pat. No. 4,623,734, in the presence of a metal-containing compound and a stabilizer. The metal-containing compound to be used in this case is selected from among oxides, acetates, maleates, succinates, nitrates, phosphates, chlorides, and sulfates of at least one metal selected from the group consisting of zinc, chromium, palladium, cobalt, nickel, iron, and aluminum. Among other compounds enumerated above, zinc acetate proved to be particularly effective. The amount of the metal-containing compound to be used is in the range of 0.005 to 0.5 mol %, preferably 0.01 to 0.1 mol %, as metal, based on 1 mol of the primary amine.

Examples of the stabilizer to be used advantageously herein include methoxy benzoquinone, p-methoxyphenol, phenothiazine, hydroquinone, alkylated diphenyl amines, methylene blue, tert-butyl catechol, tert-butyl hydroquinone, zinc dimethyldithiocarbamate, copper dimethyldithiocarbamate, copper dibutyldithiocarbamate, copper salicylate, thiodipropionic esters, mercaptobenzimidazole, triphenyl phosphite, alkylphenols, and alkylbisphenols.

Concerning the amount of the stabilizer to be added, the addition of the stabilizer in a minute amount is not sufficiently effective and the addition thereof in an unduly large amount is undesirable because it entails the drawback that the excess of stabilizer finds its way into the final product. The amount of the stabilizer to be effectively used is in the range of 0.005 to 0.5 mol %, preferably 0.05 to 0.3 mol %, based on 1 mol of the primary amine.

In accordance with the method of this invention, the former stage reaction is carried out by continuously adding the primary amine and the maleic anhydride into a mixture of the solvent and the catalyst at a temperature in the range of 100° to 250° C., preferably 110° to 220° C. and causing the water formed meanwhile by the reaction to be expelled out of the reaction system in the form of a mixture with the solvent. The molar ratio of the amount of the maleic anhydride to that of the primary amine to be added during this reaction is less than 1, preferably not less than 0.5 and less than 1, and more preferably not less than 0.7 and less than 1. This former-stage reaction is carried out, with the end point thereof fixed at the time at which the amount of the water formed by the reaction and distilled out of the reaction system reaches a total falling in the range of 40 to 99%, preferably 50 to 80%, of the theoretical amount of the water to be formed.

After the former-stage reaction is completed as described above, the (latter-stage) reaction is continued without lowering the temperature thereof by adding the maleic anhydride to the reaction system at such a rate that the molar ratio of the total amount of the maleic anhydride to be added to the reaction system to the total amount of the primary amine added to the reaction system is more than 1, desirably more than 1 and not more than 2, and more desirably more than 1 and not more than 1.3.

By heating the reaction system while keeping the water formed by the reaction distilled out of the reaction system in the form of a mixture with the solvent for a period in the range of 1 to 30 hours, preferably 0.5 to 15 hours following the start of the second addition of the maleic anhydride, the maleimide can be produced in a high yield.

The reaction of the method of this invention can be carried out effectively batchwise and continuously as well.

The solvent and the catalyst once used in the reaction may be safely used in their unmodified form in the subsequent round of the reaction.

The maleimide which is consequently obtained is a compound represented by the general formula I, for example.

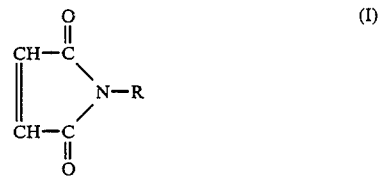

Wherein R is one member selected from the class consisting of alkyls of 1 to 20 carbon atoms, phenyl, benzyl, cyclohexyl, pyridyl, and quinolyl, and the groups possessing a hologen, a carboxyl, or a nitro substitutent. Typical examples of the maleimides include N-methyl maleimide, N-ethyl maleimide, N-n-propyl maleimide, N-isopropyl maleimide, N-n-butyl maleimide, N-sec-butyl maleimide, N-tert-butyl maleimide, N-n-hexyl maleimide, N-n-dodecyl maleimide, N-allyl maleimide, N-benzyl maleimide, N-cyclohexyl maleimide, N-phenyl maleimide, N-nitrophenyl maleimide, N-hydroxyphenyl maleimide, N-methoxyphenyl maleimide, N-ehoxyphenyl maleimide, N-monochlorophenyl maleimide, N-dichlorophenyl maleimide, N-monomethylphenyl maleimide, N-dimethylphenyl maleimide, and N-ethylphenyl maleimide. Of course, the maleimides which this invention is intended to embrace are not limited to the examples cited above.

The present invention described in detail above brings about the following advantages:

(1) Since the products of secondary reactions insoluble in the organic solvent layer occur in an extremely small amount, the separation of the catalyst layer and the organic solvent layer is attained very easily and the loss of the catalyst is substantially nil.

(2) The behavior of the catalyst is stable because of substantial absence of accumlation of impurities in the catalyst. Since the catalyst retains the property of dispersion intact through its repeated use, it permits the production to be performed in a stable yield in successive rounds of the reaction.

(3) Since the addition of the maleic anhydride enables the by-produced impurities to be decomposed once more into maleimide, the product aimed at can be obtained with high selectivity in a high yield.

(4) Since the reaction is highly selective, the maleimide can be obtained in high purity and can be refined very easily.

Now, the present invention will be described more specifically below with reference to working examples. It should be noted, however, that this invention is not restricted by these examples.

EXAMPLE 1

A flask provided with a thermometer, a condenser incorporating therein a water separator, a dropping funnel, and a stirrer was immersed in an oil bath. Into this flask were added 200 g of ortho-xylene and 20 g of ortho-phosphoric acid (containing 3 g of water). Then, the inner temperature of the flask was elevated to 130° C. by increasing the oil bath temperature and 50 g of aniline and 47 g of maleic anhydride melted at 70° C. were added dropwise into the flask over a period of 1 hour. In the meantime, the water formed by the reaction of condensation was distilled out of the reaction sytem in the form of a mixture with the ortho-xylene.

At the end of this dropwise addition, the amount of the formed water was 8.7 g, a value corresponding to 66% of the amount of water theoretically produced on the assumption that the added maleic anhydride was wholly converted into maleimide. At this point, 11 g of maleic anhydride was added to the reaction system and the reaction was continued for 4 hours.

When the 4 hours' reaction was completed, the stirrer in motion thence was stopped and the reaction mixture was allowed to separate into a catalyst layer and an ortho-xylene layer. As a result, the two layers were completely separated and absolutely no insoluble by-product was detected in the boundary between the layers. When this ortho-xylene layer was separated from the catalyst layer and then distilled under a vaucuum to expel the ortho-xylene, there was obtained 91 g of a yellow solid substance.

When this solid substance was analyzed by liquid chromatography, it was found to possess the following composition.

| | |
|---|---|
| N-phenyl maleimide | 93.4% by weight |
| Fumaric acid | Not more than 0.1% by weight |
| 2-Anilino-N-phenyl succinimide | Not more than 0.1% by weight |

The yield of N-phenyl maleimide is 91.4 mol% based on the aniline supplied for the reaciton. Control 1

The same reaction apparatus as used in Example 1 was used. Instead of supplying the maleic anhydride on two separate occasions as in Example 1, 58 g of maleic anhydride was added wholly dropwise at the outset of the reaction. The reaction was continued for 5 hours by following the procedure of Example 1, except for this fact.

After the reaction was completed, the stirrer was stopped and the reaction mixture was allowed to separate into the catalyst layer and the ortho-xylene layer. After the separation, a large amount of whitish brown by-product was found to be accumulated in the boundary between the layers. It was, therefore, extremely difficult to attain thorough separation of the ortho-xylene layer and the catalyst layer. Since the thorough separation of these two layers was extremely difficult, part of the ortho-xylene layer was removed and distilled under a vacuum to expel the ortho-xylene. Consequently, there was obtained a yellowish brown solid substance.

When this solid substance was analyzed by liquid chromatography, it was found to possess the following composition.

| | |
|---|---|
| N-phenyl maleimide | 70.3% by weight |
| Fumaric acid | 5.8% by weight |
| 2-Anilino-N-phenyl succinimide | 21.4% by weight |

It is clearly noted from the analysis that the reaction by-produced fumaric acid and 2-anilino-N-phenyl succinimide in large amounts. From this composition, the yield of the reaction is estimated to be about 69 mol %

EXAMPLE 2

In the same flask as used in Example 1, 300 g of ortho-xylene, 20g of phosphoric acid (containing 3 g of water), 0.2 g of zinc acetate, and 0.01 g of copper dibutyldithiocarbamate were placed. Then, the inner temperature of the flask was elevated to 135° C. by increasing the oil bath temperature and 50 g of aniline and 47 g of maleic anhydride melted at 70° C. were added dropwise to the contents of the flask over a period of 2 hours.

In the meantime, the water formed by the reaction of condensation was distilled out of the reaction system in the form of a mixture with the ortho-xylene. At the end of this dropwise addition, the amount of the formed water was 10.6 g, a value corresponding to 88% of the amount of water theoretically produced on the assumption that the added maleic anhydride was wholly converted into maleimide. At this stage, 16 g of maleic anhydride was added to the reaction system and the reaction was continued for 2 hours.

When the stirrer was stopped after completion of the reaction, the reaction mixture was easily separated into the catalyst layer and the ortho-xylene layer and absolutely no insoluble impurity was detected in the boundary between the two layers. When the ortho-xylene layer was separated from the catalyst layer and distilled under a vacuum to expel the ortho-xylene, there was obtained 96 g of a yellowish brown solid substance.

When this solid substance was analyzed by liquid chromatography, it was found to possess the following composition.

| N-phenyl maleimide | 95.7% by weight |
|---|---|
| Fumaric acid | Not more than 0.1% by weight |
| 2-Anilino-N-phenyl succinimide | Not more than 0.1% by weight |

The yield of N-phenyl maleimide was estimated to be 98.9 mol %, based on the supplied aniline.

EXAMPLE 3

In a flask provided with a thermometer, a condenser incorporating therein a water separator, a dropping funnel, and a stirrer, 60 g of ortho-phosphoric acid (containing 9 g of water) and 20 g of water were placed. Then, 37 g of cyclohexylamine was added thereto dropwise to synthesize a mixture of the ortho-phosphoric acid and the cyclohexyl amine salt of ortho-phosphoric acid. Subsequently, the mixture and 120 g of a granular silica gel carrier (produced by Fuji-Davison Chemical Co., Ltd. and marketed under trademark designation of "Microbead Silica Gel"), added thereto were stirred to deposit the acid on the carrier.

Then, the resultant carrier composite and 400 g of mesitylene added thereto were heated to distil out 29 g of water in combination with mesitylene and obtain a carried catalyst free of water. Then, the carrier catalyst and 0.1 g of copper bibityldithiocarbamate added thereto were heated and stirred to adjust the inner temperature of the flask to 145° C. and 100 g of cyclohexyl amine and 90 g of maleic anhydride melted at 70° C. were added dropwise thereto over a period of 1 hour. In the meantime, the water formed by the reaction was distilled out of the reaction system in combination with mesitylene.

When the reaction was continued after completion of the dropwise addition, there was formed 13 g of water, a value corresponding to 79% of the amount of water theoretically produced on the assumption that the supplied maleic anhydride was wholly converted into maleimide. Then, 12 g of maleic anhydride was added to the reaction system and the reaction was continued for 4 hours. When the stirrer was stopped after completion of the reaction, the catalyst quickly settled and the reaction mixture was separated into the mesitylene layer and the catalyst layer. Absolutely no insoluble impurity was detected in the boundary between the two layers.

Subsequently, the mesitylene layer was separated from the catalyst layer and then analyzed for the N-cyclohexyl maleimide content. As a result, the yield was found to be 98.8 mol %, based on the supplied cyclohexylamine.

EXAMPLE 4

In a beaker having an inner volume of 200 cc, 12 g of ortho-phosphoric acid (containing 2 g of water) and 40 g of silica gel (produced by Wako Junyaku K.K. and marketed under trademark designation of "Wako Gel C-100") were added in the order mentioned to effect deposition of the ortho-phosphoric acid on the silica gel.

In a flask provided with a thermometer, a condenser incorporating therein a water separator, a dropping funnel, and a stirrer, 400 g of mixed xylene and the aforementioned catalyst were placed and the inner temperature was adjusted to 135° C. Thereafter, 50 g of aniline and 47 g of maleic anhydride were added to the flask over a period of 2 hours. In the meantime, the water formed by the reaction was distilled out of the reaction system in the form of a mixture with the mixed xylene. At the end of the reaction, the amount of the formed water was 9.8 g, a value corresponding to 90% of the amount of water theoretically produced on the assumption that the supplied maleic anhydride was wholly converted into maleimide.

Then, 8 g of maleic anhydride was added to the reaction system and the reaction was continued for 3 hours. When the stirrer was stopped after completion of the reaction, the carried catalyst quickly settled below the ortho-xylene layer to induce separation of the two layers.

Absolutely no insoluble impurity was detected to accumulate in the boundary between the two layers. When this ortho-xylene layer was distilled under a vacuum to expel the ortho-xylene, there was obtained 94 g of yellow crystals. When the crystals were analyzed by liquid chromatography, they were found to posess the following composition

| N-phenyl maleimide | 97.2% by weight |
|---|---|
| Fumaric acid | Not more than 0.1% by weight |
| 2-Anilino-N-phenyl Succinimide | Not more than 0.1% by weight |

The yield of the N-phenyl maleimide is 98.3 mol %, based on the amount of the aniline supplied as a raw material for the reaction. Control 2

The reaction of Example 4 was continued for 3 hours by following the procedure of Example 4, except that the maleic anhydride used therefor was wholly added at the outset of the reaction instead of being added on two separate occasions.

When the stirrer was stopped after completion of the reaction, a yellowish white impurtiy occurred in a large amount in the boundary between the catalyt layer and the ortho-xylene layer. The boundary between the catalyst layer and the ortho-xylene layer was very obscure and the separation of these two layers was not attained.

EXAMPLE 5

The procedure of Example 4 was repeated, except that toluene was used in place of the ortho-xylene as the solvent for the reaction, the dropwise addition in the former-stage reaction was made over a period of 3 hours at the reaction temperature of 112° C., and the reaction was continued for 4 hours after completion of the dropwise addition. The amount of the water formed by the reaction by the end of the reaction was 6.1 g, a value corresponding to 47% of the amount of water theoretically produced on the assumption that the supplied maleic anhydride was wholly converted into maleimide.

Subsequently, 8 g of maleic anhydride was added to the reaction system and the latter-stage reaction was continued for 13 hours under the same conditions as in Example 4. When the stirrer was stopped after completion of the reaction, the catalyst layer and the toluene layer were clearly separated from each other and absolutely no insoluble impurity was detected therebetween. When the toluene layer was distilled to expel the toluene, there were obtained 93 g of yellow crystals.

When the crystals were analyzed by liquid chromatography, they were found to possess the following composition.

| N-phenyl maleimide | 96.1% by weight |
| --- | --- |
| Fumaric acid | Not more than 0.1% by weight |
| 2-Anilino-N-phenyl succinimide | Not more than 0.1% by weight |

The yield of this product is 96.1 mol % based on the amount of the aniline used as a raw material for the reaction.

EXAMPLE 6

A flask provided with a thermometer, a condenser incorporating therein a water separator, a dropping funnel, and a stirrer was immersed in an oil bath. Into this flask were added 100 g of p-cymene and 6 g of sulfuric acid (containing 0.1 g of water). Then, the inner temperature of the flask was elevated to 165° C. by increasing the oil bath temperature and 50 g of aniline and 42 g of maleic anhydride melted at 70° C. were added dropwise thereto over a period of 3 hours. In the meantime, the water formed by the reaction of condensation was distilled out of the reaction system in the form of a mixture with the p-cymene.

The water formed by the reaction by the completion of the dropwise addition was 6.7 g, a value corresponding to 85% of the amount of water theoretically produced on the assumption that the supplied maleic anhydride was wholly converted into maleimide. At this point, 21 g of maleic anhydride was added to the reaction system and the reaction was continued for 2 hours. When the stirrer was stopped after the 2 hours' reaction to allow the reaction mixture to separate into the catalyst layer and the p-cymene layer, the two layers were thoroughly separated from each other and absolutely no insoluble by-product was detected in the boundary therebetween. When the p-cymene layer was separated from the catalyst layer and distilled under a vacuum to expel the p-cymene, there was obtained 84 g of a yellow solid substance.

When this solid substance was analyzed by liquid chromatography, it was found to possess the following composition.

| N-phenyl maleimide | 92.1% by weight |
| --- | --- |
| Fumaric acid | Not more than 0.1% by weight |
| 2-Anilino-N-phenyl succinimide | Not more than 0.1% by weight |

The yield of the N-phenyl maleimide is 83.2 mol % based on the amount of the aniline supplied for the reaction.

EXAMPLE 7

In a beaker having an inner volume of 200 ml, 5 g of sulfuric acid (containing 0.1 g of water) and 60 g of diatomaceous earth (produced by Showa Kagaku Kogyo K.K. and marketed under trademark designation of "Radiolite") were added in the order mentioned to effect deposition of the sulfuric acid on the diatomaceous earth.

In a flask provided with a thermometer, a condenser incorporating therein a water separator, a dropping funnel, and a stirrer, 400 g of p-cymene and the aforementioned catalyst were placed and the inner temperature of the flask was adjusted to 165° C. Thereafter, 50 g of o-methyl aniline and 39 g of maleic anhydride were added thereto over a period of 3 hours. In the meantime, the water formed by the reaction was distilled out of the reaction system in the form of a mixture with the p-cymene. The amount of the formed water at the end of the addition was 5.8 g, a value corresponding to 80% of the amount of water produced theoretically on the assumption that the supplied maleic anhydride was wholly converted into maleimide.

Then, 18 g of maleic acid was added to the reaction system and the reaction was continued for 2 hours. When the stirrer was stopped after completion of the reaction, the carried catalyst quickly settled below the p-cymene layer to induce separation of the two layers. Absolutely no insoluble impurity was detected in the boundary between the two layers.

Then, the p-cymene layer was separated from the catalyst layer and analyzed for the N-(o-methylphenyl)-maleimide content. As a result, the yield was found to be 89.9 mol % based on the amount of o-methyl aniline supplied as a raw material.

EXAMPLE 8

In a beaker having an inner volume of 200 ml, 8 g of sulfuric acid (containing 0.2 g of water) and 60 g of diatomaceous earth (produced by Showa Kagaku Kogyo K.K. and marketed under trademark designation of "Radiolite") were added in the order mentioned to effect deposition of the sulfuric acid on the diatomaceous earth.

In a flask provided with a thermometer, a condenser incorporating therein a water separator, a dropping funnel, and a stirrer, 600 g of ortho-xylene, the aforementioned catalyst, and 0.2 g of phenotiazine were placed and the inner temperature of the flask was adjusted to 135° C. Thereafter, 50 g of aniline and 45 g of maleic anhydride were added thereto over a period of 6 hours. In the meantime, the water formed by the reaction was distilled out of the reaction system in the form of a mixture with the ortho-xylene. The amount of the formed water at the end of the addition was 5.9 g, a value corresponding to 70% of the amount of water theoretically produced on the assumption that the supplied maleic anhydride was wholly converted into maleimide.

Then, 18 g of maleic anhydride was added to the reaction system and the reaction was continued for 5 hours. When the stirrer was stopped after completion of the reaction, the carried catalyst quickly settled below the ortho-xylene layer to induce separation of the two layers.

At this time, absolutely no insoluble impurity was found to be accumulating in the boundary between the two layers. When ortho-xylene layer was distilled under a vacuum to expel the ortho-xylene, there were obtained 94 g of yellow crystals. When the crystals were analyzed by liquid chromatography, they were found to possess the following composition.

| N-phenyl maleimide | 93.1% by weight |
| --- | --- |
| Fumaric acid | Not more than 0.1% by weight |
| 2-Anilino-N-phenyl succinimide | Not more than 0.1% by weight |

The yield of the N-phenyl maleimide is 94.1 mol % based on the amount of the aniline used as a raw material for the reaction.

EXAMPLE 9

In a beaker having an inner volume of 200 ml, 7 g of ortho-phosphoric acid (containing 0.8 g of water) and 40 g of silica gel (produced by Wako Junyaku K.K. and marketed under trademark designation of "Wako Gel C-100") were added in the order mentioned to effect deposition of the ortho-phosphoric acid on the silica gel.

In a flask provided with a thermometer, a condenser incorporating therein a water separator, a dropping funnel, and a stirrer, 400 g of ortho-xylene, the aforementioned catalyst, and 0.2 g of dibutyl dithiocarbamate were placed and the inner temperature of the flask was adjusted to 135° C. Thereafter, 50 g of aniline and 47 g of maleic anhydride were added thereto over a period of 2 hours. In the meantime, the water formed by the reaction was distilled out of the reaction system in the form of a mixture with the ortho-xylene.

The amount of the formed water at the end of the addition was 7.3 g, a value corresponding to 75% of the amount of water theoretically produced on the assumption that the supplied maleic anhydride was wholly converted into maleimide.

Then, 11 g of maleic anhydride was added to the reaction system and the reaction was continued for 3 hours. When the stirrer was stopped after completion of the reaction, the carried catalyst quickly settled below the ortho-xylene layer to induce separation of the two layers.

At this time, absolutely no insoluble impurity was found to be accumulating in the boundary between the two layers. When the ortho-xylene layer was distilled under a vacuum to expel the ortho-xylene, there were obtained 96 g of yellow crystals. When the crystals were analyzed by liquid chromatography, they were found to possess the following composition.

| N-phenyl maleimide | 94.6% by weight |
|---|---|
| Fumaric acid | Not more than 0.1% by weight |
| 2-Anilino-N-phenyl succinimide | Not more than 0.1% by weight |

The yield of the N-phenyl maleimide is 97.7 mol % based on the amount of the aniline used as a raw material for the reaction.

EXAMPLE 10

A flask provided with a thermometer, a condenser incorporating therein a water separator, a dropping funnel, and a stirrer was immersed in an oil bath. Into this flask were added 300 g of ortho-xylene and 7 g of pyrophosphoric acid.

Then, the inner temperature of the flask was elevated to 135° C. by increasing the oil bath temperature and 50 g of o-chloroaniline and 37 g of maleic anhydride melted at 70° C. were added dropwise into the flask over a period of 1 hour. In the meantime, the water formed by the reaction of condensation was distilled out of the reaction system in the form of a mixture with the ortho-xylene. The amount of the formed water at the end of water was 4.1 g, a value corresponding to 58% of the amount of water theoretically produced on the assumption that the supplied maleic anhydride was wholly converted into maleimide.

After the dropwise addition, 3 g of maleic anhydride was added to the reaction system and the reaction system and the reaction was continued for 3 hours. When the stirrer was stopped after completion of the reaction, the catalyst quickly settled to induce separation of the ortho-xylene layer and the catalyst layer. Absolutely no insoluble impurity was found to occur in the boundary therebetween.

Then, the ortho-xylene layer was separated from the catalyst layer and analyzed for the N-(o-chlorophenyl)-maleimide content. Consequently, the yeild was found to be 88.7 mol % based on the amount of the o-chloroaniline used as a raw material.

EXAMPLE 11

In a beaker having an inner volume of 200 ml, 15 g of pyrophosphoric acid and 40 g of silica gel (produced by Wako Junyaku K.K. and marketed under trademark designation of "Wako Gel C-100") were added in the order mentioned to induce deposition of the pyrophosphoric acid on the silica gel.

In a flask provided with a thermometer, a condenser incorporating therein a water separator, a dropping funnel, and a stirrer, 300 g of ortho-xylene, the aforementioned catalyst, and 0.1 g of phenothiazine were placed and the inner temperature of the flask was adjusted to 135° C. Thereafter, 50 g of aniline and 50 g of maleic anhydride were added thereto over a period of 1 hour. In the meantime, the water formed by the reaction was distilled out of the reaction system in the form of a mixture with the ortho-xylene. The amount of the formed water at the end of the addition was 5.9 g, a value corresponding to 62% of the amount of water theoretically produced on the assumption that the supplied maleic anhydride was wholly converted into maleimide.

Then, 5 g of maleic anhydride was added to the reaction system and the reaction was continued for 3 hours. When the stirrer was stopped after completion of the reaction, the carried catalyst quickly settled below the ortho-xylene layer to induce separation of the two layers.

Absolutely no insoluble impurity was found to be accumulating in the boundary between the two layers. When the ortho-xylene layer was distilled under a vacuum to expel the ortho-xylene, there were obtained 94 g of yellow crystals. When the crystals were analyzed by liquid chromatography, they were found to possess the following composition.

| N-phenyl maleimide | 92.2% by weight |
|---|---|
| Fumaric acid | Not more than 0.1% by weight |
| 2-Anilino-N-phenyl succinimide | Not more than 0.1% by weight |

The yield of the N-phenyl maleimide is 93.2 mol % based on the amount of the aniline used as a raw material for the reaction.

EXAMPLES 12 TO 17

The reaction was carried out by following the procedure of Example 1, except that the molar ratio of the reactants for the reactions was varied as indicated in Table 1. The results were as shown in Table 1.

TABLE 1

| Example | Reaction ratio *1 | Reaction ratio *2 | Yield | Condition of boundary between catalyst and reaction solution | Maleimide composition after reaction | |
|---|---|---|---|---|---|---|
| | | | | | N-phenyl maleimide | 2-Anilino-N-phenyl succinimide |
| Example 12 | 0.80 | 1.02 | 89.2 | No insoluble impurity | 90.3 wt % | max. 0.1 wt % |
| Example 13 | 0.90 | 1.02 | 90.4 | No insoluble impurity | 90.8 wt % | max. 0.1 wt % |
| Example 14 | 0.90 | 1.05 | 91.1 | No insoluble impurity | 91.1 wt % | max. 0.1 wt % |
| Example 15 | 0.90 | 1.08 | 91.2 | No insoluble impurity | 92.5 wt % | max. 0.1 wt % |
| Example 16 | 0.95 | 1.10 | 92.3 | No insoluble impurity | 92.6 wt % | max. 0.1 wt % |
| Example 17 | 0.98 | 1.10 | 92.2 | No insoluble impurity | 92.3 wt % | max. 0.1 wt % |
| Control 3 | 1.05 | 1.05 | about 73 | Whitish brown insoluble occurred heavily to render separation of the catalyst and the reaction solution difficult | 74.2 wt % | 20.4 |

*1 Maleic anhydride/aniline (molar ratio) in former-stage reaction.
*2 Total amount of maleic anhydride added to the reaction system in the former-stage reaction/total amount of aniline added to the reaction system (molar ratio)

What is claimed is:

1. A method for the production of maleimides from maleic anhydride and a primary amine by heating in a water soluble or water-immiscible, reaction-inert, azeotropic, organic solvent containing an acid catalyst, which comprises effecting a first-stage reaction by adding said maleic anhydride and said primary amine contemporaneously in amounts such that the molar ratio of said maleic anhydride to said primary amine is 0.5 less than 1 and subsequently carrying out a second-stage reaction by adding to the reaction system a further amount of maleic anhydride in an amount such that the final molar ratio of the total amount of maleic anhydride to be added to said reaction system to the amount of said primary amine added to said reaction system is between 1:1 and 2:1, said first-stage reaction being performed from the time the reaction is started till the time the water formed by the reaction is azeotroped out in an amount in the range of 40 to 99% of the theoretical amount of water to be formed and then the second-stage reaction is carried out until completion of the reaction, and said first-stage and second-stage reactions being carried out at a temperature in the range of 100° to 250° C.

2. A method according to claim 1, wherein said latter-stage reaction is carried out for a period in the range of 1 to 30 hours.

3. A method according to claim 1, wherein said former-stage reaction is carried out from the time the reaction is started till the time the water formed by the reaction is distilled out in an amount in the range of 50 to 80% of the theoretical amount of water to be formed.

4. A method according to claim 1, wherein said former-stage and latter-stage reactions are carried out at a temperature in the range of 110° to 220° C.

5. A method according to claim 1, wherein the molar ratio of said maleic anhydride to said primary amine in said former-stage reaction is not less than 0.7 and less than 1 and the molar ratio of the total amount of said maleic anhydride to be added to the reaction system to the total amount of said primary amine added to the reaction system in said latter-stage reaction is more than 1 and not more than 1.3.

6. A method according to claim 1, wherein the amount of said acid catalyst is in the range of about 2 to about 400 mol %, based on the amount of the primary amine to be used.

7. A method according to claim 6, wherein the amount of said solvent is in the range of about 1 to about 40 times the amount of said primary amine to be used.

8. A method according to claim 1, wherein said catalyst is a catalyst carried on a solid carrier.

9. A method according to claim 1, wherein said former-stage reaction and latter-stage reaction are carried out in the presence of a metal-containing compound and a stabilizer.

10. A method according to claim 9, wherein the amount of said metal-containing compound is in the range of 0.005 to 0.5 mol %, based on the amount of said primary amine and the amount of said stabilizer is in the range of 0.005 to 0.5 mol % based on the amount of said primary amine.

11. A method according to claim 1, wherein said maleimide is represented by the formula I:

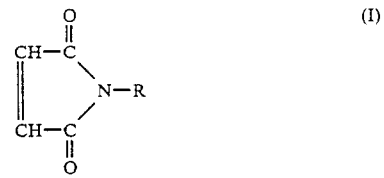

wherein R is selected from the group consisting of substituted and unsubstituted alkyls of 1 to 20 carbon atoms, phenyl, benzyl and cyclohexyl and said substituents being selected from the group consisting of halogen, and nitro.

12. A method according to claim 11, wherein said maleimide is N-phenyl maleimide or N-cyclohexyl maleimide.

* * * * *